(12) United States Patent
Bick

(10) Patent No.: US 10,433,534 B2
(45) Date of Patent: Oct. 8, 2019

(54) DISCRIMINATORY INSECT SAMPLING DEVICE AND METHOD FOR USE

(71) Applicant: Emily Nicole Bick, Davis, CA (US)

(72) Inventor: Emily Nicole Bick, Davis, CA (US)

( * ) Notice: Subject to any disclaimer, the term of this patent is extended or adjusted under 35 U.S.C. 154(b) by 55 days.

(21) Appl. No.: 15/732,530

(22) Filed: Nov. 22, 2017

(65) Prior Publication Data

US 2018/0146656 A1 May 31, 2018

Related U.S. Application Data

(60) Provisional application No. 62/497,613, filed on Nov. 25, 2016.

(51) Int. Cl.
*A01M 1/10* (2006.01)
*A01M 1/20* (2006.01)
*A01M 13/00* (2006.01)
*G01N 1/02* (2006.01)

(52) U.S. Cl.
CPC .............. *A01M 1/10* (2013.01); *A01M 1/20* (2013.01); *A01M 1/2038* (2013.01); *A01M 13/003* (2013.01); *G01N 1/02* (2013.01); *A01M 13/00* (2013.01); *A01M 2200/01* (2013.01)

(58) Field of Classification Search
CPC ........ A01M 1/10; A01M 1/20; A01M 1/2038; A01M 13/00; A01M 13/003; A01M 2200/01
See application file for complete search history.

(56) References Cited

U.S. PATENT DOCUMENTS

| 5,063,706 A * | 11/1991 | Aki | ........................ A01G 9/18 43/124 |
| 6,766,612 B1 * | 7/2004 | Liu | ..................... A01M 13/003 43/125 |
| 2002/0078621 A1 * | 6/2002 | Jones | .................. A01M 1/2038 43/124 |

(Continued)

FOREIGN PATENT DOCUMENTS

| CA | 2489273 A1 * | 12/2003 | .......... A01M 1/2055 |
| DE | 4037925 A1 * | 5/1991 | .......... A01M 13/003 |

OTHER PUBLICATIONS

Arbab A.,et al 2014. Spatial distribution and sequential sampling plans for adult Sitona humeralis . . . in alfalfa. Journal of Asia Entomology 17: 515-519.

(Continued)

*Primary Examiner* — Ryan A Reis

(57) ABSTRACT

Present invention is a device and a method for collecting targeted insects or targeted insect communities on plants. It can be used to non-destructively collect insect communities from a single plant. Alternatively, it can be used to collect a targeted insect from a plant. Present invention consists of the following elements: a first hose; an extended air nozzle; a thumb lever push valve; a brass barb; a second hose; a knapsack; a pneumatic mini timer; a carbon dioxide flow regulator; a carbon dioxide tank; a bag; a drawstring; and a glass vial. The present invention can be used as follows: consulting a chart; setting carbon dioxide flow regulator; setting pneumatic mini timer; deploying a bag over a plant; cinching said bag; depressing thumb lever; shaking bag to relocate targeted insects from bag into the glass vial; detaching glass vial; and capping glass vial.

2 Claims, 1 Drawing Sheet

(56) References Cited

U.S. PATENT DOCUMENTS

| | | | | |
|---|---|---|---|---|
| 2005/0108922 A1* | 5/2005 | Bianchini | ............ | A01M 1/2038 43/132.1 |
| 2012/0186138 A1* | 7/2012 | Bell | .................... | A01M 13/003 43/125 |
| 2016/0262372 A1* | 9/2016 | Kunz | .................... | A01M 13/00 |

OTHER PUBLICATIONS

Athanassiou, C. et al. 2001.Detection of stored-wheat beetle species and estimation of population density using unbaited . . . Entomologia experimentalis et applicata 98: 67-78.

Athanassiou, C., C. Nansen, and B. Vayias. 2010. Spatial and non-spatial analyses of insect counts in bulk-stored barley. Bulletin of entomological research 100: 395-403.

Badre, N. H. et al. 2005. The physiological and behavioral effects of carbon dioxide on Dros . . . Comparative Biochem & PhysiolPart A: Molecular Integr Physiology 140: 363-376.

Bannerman J., A. et al. 2015. Comparison of relative bias, precision, and efficiency of sampling methods for natural enemies of soybean aphid . . . J. Econ. Entom 108: 1381-97.

Cabrini, I., C. et al. 2016. A simple method for immobilising small dipteran insects and its validation for Aedes aegypti. Entomologia Experimentalis et Applicata 160: 96-100.

Castle, S., et al. 2009. Sampling plans, selective insecticides and sustainability: the case for IPM as 'informed pest management'. Pest Mgmt Science 65: 1321-28.

Cushing, J. M. 1998. An introduction to structured population dynamics, SIAM.

Dara, S. K. 2015. Virus decline of strawberry in California and the role of insect vectors and associated viruses. Plant Health Prog 16: 211-215.

Fleischer, S. et al. 1999. Sampling in precision IPM: when the objective is a map. Phytopathology 89: 1112-1118.

Fusaro, S., F. et al. 2016. Higher efficiency in organic than in conventional management of biological control in horticultural crops in N.E. Italy. Biol.Ctl. 97:89-101.

Hassell, M. P. et al. 1991. Spatial structure and chaos in insect population dynamics. Nature 353: 255-258.

Lloyd, M. et al. 2016. Growing for the future: Collective action, land stewardship and soilborne pathogens in California strawberry production. California Agricult. 70:101-103.

Nilson, T. L. et al. 2006. The effects of carbon dioxide anesthesia and anoxia on rapid cold-hardening and chill coma recovery in *Drosophila* . . . J. Insect Physiol. 52:1027-33.

Osborne, K. H. et al. 1999. Allen-Vac: An Internal Collection Bag Retainer Allows for Snag-Free Arthropod Sampling in Woody Scrub. Environmental entomology 28: 594-596.

Pérez-Rodriguez, J. et al. 2017. Aggregation Patterns, Sampling Plan, and Economic Injury Levels for the New Citrus Pest *Delottococcus* . . . Journal of Economic Entomology.

Rancourt, B. et al. 2000. Circadian activity of Lygus lineolaris (Hemiptera: Miridae) and effectiveness of sampling techniques in strawberry fields. J. econ. entom. 93:1160-66.

Roubos, C. R. et al. 2014. Mitigating the effects of insecticides on arthropod biological control at field and landscape scales. Biological control 75: 28-38.

Seelan S. K. et al. 2003. Remote sensing applications for precision agriculture: A learning community approach. Remote Sensing of Environment 88: 157-169.

Stern, V. et al. 1959. The integration of chemical and biological control of the spotted alfalfa aphid: the integrated control concept. California Agriculture 29: 81-101.

Swezey, S. L. et al. 2014. Control of western tarnished plant bug *Lygus hesperus* Knight (*Hemiptera: Miridae*) in Calif. organic strawberries using . . . Environ'l Entom. 36:1457-65.

Tuan, S.-J. et al. 2016. Predatory efficacy of Orius strigicollis (Hemiptera: Anthocoridae) against Tetranychus urticae (Acarina: Tetranychidae) . . . J. Asia-Pac Entom.19:109-14.

Zalom, F. et al. 2014. UC IPM pest management guidelines: strawberry. Univ. of Calif. Statewide Integrated Pest Management Program. Oakland: UC ANR Publ. 3468.

Zalom, F. G. et al. 1993. Sampling for Lygus hesperus (*Hemiptera: Miridae*) in strawberries. Journal of economic entomology 86: 1191-95.

Zou, Y. et al 2016. Modification and Application of a Leaf Blower-vac for Field Sampling of Arthropods. Journal of Visualized Experiments: JoVE.

\* cited by examiner

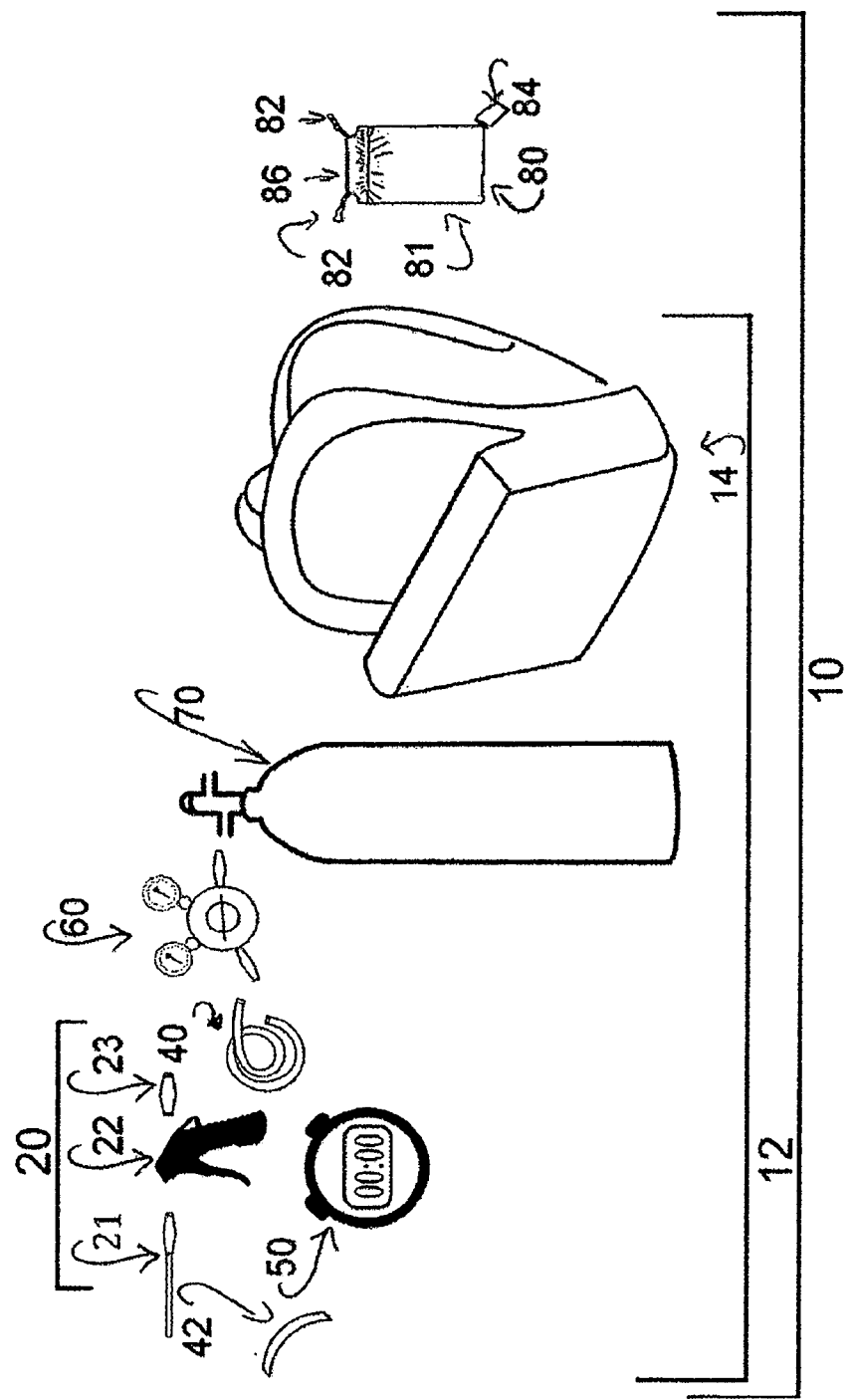

DISCRIMINATORY INSECT SAMPLING DEVICE AND METHOD FOR USE

BACKGROUND OF THE INVENTION

Field of the Invention

The present disclosure relates to the field of insect sampling devices. More particularly, the present invention is a device and method designed to capture insects or insect communities particularly targeted by the device user.

Background Art

Insect sampling can provide useful information for insect population dynamics. Sampling of insect pests and adjacent insect communities assists with successful implementation of integrated pest management.

An accurate estimation of pest population dynamics is needed to implement successful and sustainable integrated pest management (IPM) strategies in agroecosystems (Hassell et al. 1991, Castle and Naranjo 2009). Specifically, an accurate estimation of pest population dynamics is integral to the precision targeting of pests (Stern et al. 1959, Fleischer et al. 1999, Pérez-Rodriguez et al. 2017), where precision agriculture is defined as variable management based on site-specific conditions (Seelan et al. 2003). This precision IPM approach results in a reduction of pesticide use and rate of resistance development (Fleischer et al. 1999, Roubos et al. 2014). However, to do so, the spatial and temporal variation of the pest population dynamics needs to be characterized through sampling.

Thus, the development of a more accurate and less costly insect sampling technique will allow for more economically efficient information while reducing risk associated with variability or underestimation. Current widely used insect sampling methods in agriculture include sweep net sampling and plant vacuuming. These insect sampling methods have been found to be consistent but result in an underestimate of insect populations (Zalom et al. 1993).

There is a high demand for feasible, practical, and reliable sampling methods to monitor population dynamics of pests and their natural enemies (Cushing 1998, Roubos et al. 2014). Accurate sampling is particularly useful in high-value horticultural crops where pest outbreaks may result in significant yield loss (Fusaro et al. 2016). The western tarnished plant bug (*Lygus hesperus* Knight, Hemiptera: Miridae), on California strawberries (*Fragaria* x *ananassa* Duchesne, Rosales: Rosaceae) is such a pest (Swezey et al. 2014).

Pest population dynamics are monitored using three main sampling methods: sweepnet sampling, portable aspirator sampling, and tapping flower clusters. These sampling methods result in a consistent but underestimated forecast of western tarnished plant bug and other pest populations (Zalom et al. 1993).

More particularly, sweep net sampling and plant vacuuming is destructive to plants because the former uses physical pressure which causes plant leaves to tear or detach and fruit or flowers to be separated from the plant and the latter uses a vacuum which causes plant leaves to be torn or detached and fruit of flowers to be separated from the plant. The portable aspirator method is noted as time-consuming, and the tapping flower clusters method is biased towards collecting immature insects (Rancourt et al. 2000) and sweepnets are unable to penetrate into shrubs (Osborne and Allen 1999) rendering them inadequate in this system.

Also, these methods over-represent prominent pests, while under-representing natural enemies (Bannerman et al. 2015). Moreover, sweep net sampling and plant vacuuming methods involve killing the sampled insects. Furthermore, plant vacuuming disturbs insect populations prior to collection due to sound and vibration which decreases sampling accuracy. Additionally, plant vacuuming disproportionally minimizes collection of small insects due to the fact that the suction destroys the smallest insects before they are collected.

An alternative insect sampling method is the use of carbon dioxide ($CO_2$) gas to anesthetize insects. $CO_2$ gas is used as an insect anesthetic in many laboratories (Nilson et al. 2006). The dosage and exposure time necessary to anesthetize an insect is likely species-specific (Cabrini et al. 2016). Carbon dioxide gas exposure in an enclosed area may be varied by changing the duration and pressure of a carbon dioxide gas discharge source. Thus, selective insect sampling can be implemented in the field by properly calibrating a carbon dioxide gas discharge source and associated enclosure to anesthetize an insect species or insect communities of interest.

Such an insect sampling technique is superior to sweep net sampling, beat tray sampling, and plant vacuuming because it does not harm plants, allows for operator efficiency by only collecting the targeted insects, and increasing the accuracy by overcoming the under-estimation problem.

Specifically, the present invention teaches a device which commercializes the relationship between $CO_2$ pressure and duration of exposure and insect anesthetization, defined as a reversible loss of mobility (Nilson et al. 2006). The present invention teaches that an increase in $CO_2$ exposure results in a decrease in time until an insect becomes anesthetized.

Advantages of the Current Invention

The present invention substantially fulfills the foregoing unmet needs of prior art. The present invention is composed of the following elements: a first hose; an air nozzle; a push valve; a brass barb; a second hose; a knapsack; a pneumatic mini timer; a carbon dioxide flow regulator; a carbon dioxide tank; a bag; a drawstring; a chart containing paired data for capturing target insects, specifically the appropriate rate and duration of carbon dioxide flow, at different bag volumes; a glass vial.

BRIEF DESCRIPTION OF THE DRAWINGS

The invention will be better understood and objects other than those set forth above will become apparent when consideration is given to the following detailed description thereof. Such description makes reference to the annexed drawings herein:

FIG. 1 is a description of the current invention.

DETAILED DESCRIPTION OF THE INVENTION

The present invention teaches a Discriminatory Insect Collection Device and a method for use. With reference to FIG. 1, the current invention 10 has two main elements, namely the carbon dioxide dispensing system 12 and the insect collection system 80. The carbon dioxide dispensing system 12 is composed of two elements outside the knapsack 14, namely the nozzle 20 and hose system 40. The nozzle 20 is composed of three elements, namely the extended air nozzle 21, the thumb Lever push valve 22, and the brass barb 23. Nozzle 20 is attached to hose 40. Hose 40 is attached to carbon dioxide dispensing system 12. Carbon dioxide dispensing system 12 is partially contained in a knapsack 14. Carbon dioxide dispensing system 12 contained within the knapsack 14 is composed of four elements, namely the pneumatic mini timer 50, the hose 42, the carbon dioxide flow regulator 60, and the carbon dioxide tank 70. Hose 40 is attached to the pneumatic mini timer 50, which is attached to hose 42, which is attached to carbon dioxide flow regulator 60, which is attached to the carbon dioxide tank 70. Insect collection system 80 is composed of three elements, namely bag 81, drawstring 82, and glass vial 84. Bag 81 has a drawstring 82 surrounding opening 86. Opening 86 is distal to glass vial 84.

In the preferred embodiment, the current invention 10 weighs between three (3) and 20 pounds. The carbon dioxide dispensing system 12 dispenses carbon dioxide at a rate of between 20 and 75 liters per minute. Nozzle 20 is made of plastic and aluminum. The hose system 40 should be 0.5 inches in diameter, between one and three feet long and composed of polyethylene. The extended air nozzle 21 is composed of aluminum. The thumb lever push valve 22 is composed of plastic. The brass barb 23 is a ¼Npt×¼ brass barb. The carbon dioxide dispensing system 12 is contained in a traditional knapsack made of nylon with hull suitable for passing hose 40 from carbon dioxide dispensing system 12 to pneumatic mini timer 50. The pneumatic mini timer 50 is capable of accepting a continuous air input signal and calibrated to one particular task, namely adjusting limiting the time of the carbon dioxide flow. Said flow is typically between two (2) seconds and two minutes. The hose 42 should be 0.5 inches in diameter, between one and three feet long and composed of polyethylene. The carbon dioxide flow regulator 60 is usually a low-cost gas flow meter and regulator for carbon dioxide. The carbon dioxide tank 70 weighs between one (1) and 20 pounds and serves to hold pressurized carbon dioxide. The bag 81 is made of a light weight plastic drawstring bag. Bag 81 has a drawstring 82, made of flexible plastic ribbon (such as the drawstring on a commercially available four (4) liter trash bag) which is capable of cinching around the stem or stems of a plant and extended air nozzle 21 in such a way as to contain the carbon dioxide being dispense by nozzle 20. Bag 81 is typically one (1) to 20 liters in volume. Bag 81 has a glass vial 84 distal from opening 86. Glass vial 84 is composed of a commercially available laboratory glass vial with a volume capacity between two (2) milliliters and 40 milliliters. Glass vial 84 is detachable from bag 81.

Insects are susceptible to being anesthetized by carbon dioxide exposure. Insects vary in characteristics. One characteristic is the amount of carbon dioxide exposure necessary for insect anesthetization.

For example, a cockroach is able to close its spiracles and therefore elongate time until anesthetization for as long as ten minutes of high levels of carbon dioxide exposure. Whereas thrips do not have this ability and are typically anesthetized within five (5) seconds of low level carbon dioxide exposure.

Carbon dioxide exposure in the present invention can be varied by changing bag 81 volume, rate of carbon dioxide flow as allowed by carbon dioxide flow regulator 60, and the duration of carbon dioxide flow as allowed by pneumatic mini timer 50. For the present invention, the combination of the three factors, bag 81 volume, rate of carbon dioxide flow as allowed by carbon dioxide flow regulator 60, and the duration of carbon dioxide flow as allowed by pneumatic mini timer 50, are known as paired data because each element is paired with two others for the purposes of capturing target insects or insect communities in a discriminatory manner. Experimental data is necessary to determine appropriate bag 81 volume, rate of carbon dioxide flow as allowed by carbon dioxide flow regulator 60, and the duration of carbon dioxide flow as allowed by pneumatic mini timer 50 to capture the target insect. For example, two seconds of 25 liters per minute of carbon dioxide flow in a three-liter bag was appropriate for capturing 95% of thrips on a strawberry plant. However, eight seconds of 25 liters per minute of carbon dioxide flow in a three-liter bag was appropriate for capturing 95% of aleyrodidae insects. As a further example, two seconds of 50 liters per minute of carbon dioxide flow in a three-liter bag was appropriate for capturing 95% of carabidae insect.

When experimental data is not available, the present invention user can rely upon a generalized chart. For example, below please find a generalized chart for a three-liter bag for tiny, medium sized, and large insects. Consult chart which is a matrix of time and rate suitable for anesthetize target insect.

Generalized Chart of Paired Data for Three-Liter Bag Volume

| Insect Size | 25 liters per minute | 50 liters per minute |
| --- | --- | --- |
| Tiny (ex. Thrips) | 2 seconds | 8 seconds |
| Mid (ex. Aleyrodidae) | 8 seconds | 2 seconds |
| Large (ex. Carabidae) | 8 seconds | 2 seconds |

This generalized chart can be adjusted to different bag volumes by scaling the rate of carbon dioxide flow as allowed by carbon dioxide flow regulator 60, or the duration of carbon dioxide flow as allowed by pneumatic mini timer 50 applying a scaling factor of (new bag volume)/(three liters) to either the rate of carbon dioxide flow or the duration of carbon dioxide flow. For example, when using a bag with a ten-liter volume and targeting large insects, a scaling factor of 10/3 can be applied to either the rate of carbon dioxide flow or the duration of carbon dioxide flow. This would result in either the use of a 83.33 liter per minute rate of carbon dioxide flow with eight seconds of carbon dioxide duration or the use of a 25 liter per minute rate of carbon dioxide flow with 26.66 seconds of carbon dioxide duration.

To use device 10, set carbon dioxide flow regulator 60 for specified rate and set pneumatic mini timer 50 for specified time. Place bag 81 over the plant and extended air nozzle 21, cinching it with drawstring 82. After said cinching, depressing thumb lever push valve 22 resulting in adding carbon dioxide to bag 81 in accordance with settings on the carbon dioxide flow regulator 60 and pneumatic mini timer 50. Shake bag 81 to relocate targeted insects from bag 81 into the glass vial 84 and detach and cap glass vial 84.

For example, the present invention can be used for the following application: in a strawberry agroecosystem containing both alfalfa and strawberry plants, for collecting the major pest western tarnished plant bug (*Lygus hesperus*, Hemiptera: Miridae) and its associated insect natural enemy community from both plant species.

Another example for application of the present invention is the mass collection of multiple mosquito (Diptera) species from shrub foliage for the purpose of determining vectoral capacity during an epidemiological health crisis.

The present invention and method surmounts short comings noted above in the prior art by using carbon dioxide, rather than physical netting, beating a plant canopy, or vacuuming to capture insects. In particular, while the prior art methods collect a group of insects, the present invention collects a specifically targeted insect species. Alternately, the present invention can selectively capture an entire insect community on a plant by anesthetizing and capturing all the insects, while the prior art suffers from the shortcoming of scaring away part of the insect community through disturbances such as air vibrations, extraneous noise, and physical plant disturbances.

The present invention overcomes the plant damage caused by prior art collection methods by not physically disrupting the plant. The present invention is capable of capturing live or dead insects, whereas the prior art devices and methods rely on capture methods which destroy or kill the insects.

Although the invention has been described in detail in the foregoing embodiments for the purpose of illustration, it is to be understood that such detail is solely for that purpose, and that variations can be made therein by those skilled in the art without departing from the spirit and scope of the invention, except as it may be described by the following claims.

What is claimed is:

1. A discriminatory insect sampling device comprising:
   a nozzle having an extended air nozzle, a thumb lever push valve, and a brass barb;
   a pneumatic mini timer connected to the nozzle by a first hose;
   a carbon dioxide flow regulator connected to the pneumatic mini timer by a second hose, wherein the carbon dioxide flow regulator is attached to a carbon dioxide tank;
   a bag having a drawstring; and
   a glass vial attached to the bag, wherein the nozzle is configured to introduce carbon dioxide into the bag.

2. A method for using the device of claim 1 comprising:
   reading a chart to determine a specified time and a specified rate of carbon dioxide flow suitable to anesthetize a target insect;
   setting the carbon dioxide flow regulator for the specified rate;
   setting the pneumatic mini timer for the specified time;
   placing the bag over a plant and the extended air nozzle;
   cinching the bag with the drawstring;
   depressing the thumb lever push valve to add carbon dioxide to the bag in accordance with the settings on the carbon dioxide flow regulator and the pneumatic mini timer;
   shaking the bag to relocate targeted insects from the bag into the glass vial; and
   detaching the glass vial from the bag; and capping the glass vial.

* * * * *